US012612362B2

(12) United States Patent
Zhang et al.

(10) Patent No.: US 12,612,362 B2
(45) Date of Patent: Apr. 28, 2026

(54) ANISOMYCIN DERIVATIVE AND USE OF ANISOMYCIN AND DERIVATIVE THEREOF AS GLP-1R AGONIST

(71) Applicant: SHANXI MEDICAL UNIVERSITY, Shanxi (CN)

(72) Inventors: Yi Zhang, Shanxi (CN); Huan Xue, Shanxi (CN); Min Zhang, Shanxi (CN); ZhiHong Lu, Shanxi (CN); Linping Zhi, Shanxi (CN); Zhitong Wen, Shanxi (CN); Lijuan Cui, Shanxi (CN); Tao Bai, Shanxi (CN); Yunfeng Liu, Shanxi (CN)

(73) Assignee: SHANXI MEDICAL UNIVERSITY, Taiyuan (CN)

( * ) Notice: Subject to any disclaimer, the term of this patent is extended or adjusted under 35 U.S.C. 154(b) by 406 days.

(21) Appl. No.: 18/357,985

(22) Filed: Jul. 24, 2023

(65) Prior Publication Data

US 2023/0365498 A1 Nov. 16, 2023

Related U.S. Application Data

(63) Continuation-in-part of application No. PCT/CN2021/096473, filed on May 27, 2021.

(30) Foreign Application Priority Data

Jan. 26, 2021 (CN) ......................... 202110103556.3

(51) Int. Cl.
*C07D 207/46* (2006.01)
*A61P 3/10* (2006.01)

(52) U.S. Cl.
CPC .............. *C07D 207/46* (2013.01); *A61P 3/10* (2018.01)

(58) Field of Classification Search
CPC ................................ C07D 207/46; A61P 3/10
See application file for complete search history.

(56) References Cited

U.S. PATENT DOCUMENTS 5,463,078 A 10/1995 Iino et al.

FOREIGN PATENT DOCUMENTS

JP S6289659 A 4/1987

OTHER PUBLICATIONS

Grollman (The Journal of Biological Chemistry, 1967, vol. 242, No. 13, p. 3226-3233) (Year: 1967).*

Wong et al. (Canadian Journal of Chemistry, 1971, vol. 49, p. 639-643) (Year: 1971).*

Zhou et al. (Organic Letters, 2010, vol. 12, No. 9, p. 2104-2107) (Year: 2010).*

Yin et al. (Stem Cell Research & Therapy, 2020, 11:49, 16 pages) (Year: 2020).*

Li, Ji et al., "Concise synthesis of (−)-anisomycin.", Chinese Chemical Letters, vol. 23, No. 6, May 12, 2012; ISSN:1001-841; pp. 647-649.

Kaden, Silvia et al., "Syntheses of Enantiomerically Pure 2-Substituted Pyrrolidin-3-ones via Lithiated Alkoxyallenes—An Auxiliary-Based Synthesis of both Enantiomers of the Antibiotic Anisomycin", Helvetica Chimica Acta, vol. 88, No. 7, Jul. 20, 2005; ISSN:1522-2675; pp. 1826-1838.

Rosser, Edward M. et al., "Synthetic anisomycin analogues activating the JNK/SAPK1 and p38/SAPK2 pathways"; Organic & Biomolecular Chemistry; vol. 2, No. 1, Dec. 2, 2003; ISSN:1477-0539; pp. 142-149.

Schwardt, Oliver et al., "Stereoselective Synthesis and Biological Evaluation of Enisomycin and 2-Substituted Analogs.", Synthesis; vol. 1999, No. SI, Aug. 31, 1999; ISSN:0039-7881; pp. 1473-1490.

Tokuda, Masao et al.; "New Total Synthesis of (+)-N-Methylanisomycin by Anodic Cyclization of δ-Alkenylamine", Tetrahedron, vol. 49, No. 12, Mar. 19, 1993; ISSN:0040-4020; pp. 2413-2426.

Chang, Shen et al.; "Systems Approach to Pathogenic Mechanism of Type 2 Diabetes and Drug Discovery Design Based on Deep Learning and Drug Design Specifications", International Journal of Molecular Sciences, vol. 22, No. 166, Dec. 26, 2020; ISSN:1422-0067; pp. 1-33.

American Chemical Societyacs, "STNext Registry database", http://www.stn.org; Jun. 15, 1985; CAS RN 96740-19-1 96751-33-6 96740-17-9 96740-18-0.

* cited by examiner

*Primary Examiner* — James D. Anderson
(74) *Attorney, Agent, or Firm* — NKL Law; Allen Xue

(57) ABSTRACT

The present invention relates to an anisomycin derivative represented by general formula (I) or pharmaceutically acceptable salts, solvates and stereoisomers thereof. According to the present invention, it is found that anisomycin and derivatives thereof have the effect of promoting insulin secretion under high blood sugar concentrations, and can treat diabetes and prevent the occurrence of hypoglycemia. It is found, by studying its mechanism of action, that the anisomycin derivative is highly related to GLP-1R, indicating that the anisomycin derivative is a small molecule GLP-1R agonist, which can effectively treat a variety of GLP-1R-mediated diseases including obesity and diabetes, and has good commercial application prospects and scientific research value.

5 Claims, 7 Drawing Sheets

ANISOMYCIN DERIVATIVE AND USE OF ANISOMYCIN AND DERIVATIVE THEREOF AS GLP-1R AGONIST

TECHNICAL FIELD

The invention belongs to the technical field of medicine, and particularly relates to an anisomycin derivative, and use of anisomycin and a derivative thereof as a GLP-1R agonist.

BACKGROUND

Glucagon-like peptide-1 (GLP-1) is secreted by L cells in the gastrointestinal tract and exerts a hypoglycemic effect following the intake of glucose and other nutrients. Studies on the physiological effects of GLP-1 have shown that GLP-1 can not only enhance insulin secretion from β-cells, but also reduce glucagon secretion by acting on α-cells, thereby reducing glycogen output; and GLP-1 acts on the central nervous system and stomach to suppress appetite and slow down gastric emptying, thereby reducing β-cell load, etc. However, since GLP-1 is rapidly degraded by dipeptidyl peptidase 4 (DPP-4) in vivo, its duration of action is limited. Therefore, the current GLP-1-based methods to improve blood sugar control include exogenous drugs that mimic the effect of GLP-1 and prolong the activity of endogenous GLP-1. GLP-1 receptor agonists play the hypoglycemic effect based on this.

So far, traditional drugs used clinically to treat type 2 diabetes (T2DM), such as insulin and sulfonylureas, can effectively reduce hyperglycemia, but after blood sugar is controlled in a normal range, can still continue to exert hypoglycemic effects, which leads to a risk of hypoglycemia in T2DM patients. Studies have reported that GLP-1 receptor agonists stimulate insulin secretion in a glucose concentration-dependent manner through the GLP-1 receptor (GLP-1R), which is the greatest advantage of the GLP-1 receptor agonists over other hypoglycemic drugs, so that the risk of hypoglycemia can be avoided. In addition, the GLP-1 receptor agonists have some effects other than hypoglycemic effect, including weight loss, cardiovascular benefits, improvement of Alzheimer's disease and fatty liver, etc.

As a hormone secreted from intestinal cells stimulated by eating, incretin can regulate the response of insulin to eating, and its insulin secretion-stimulating effect accounts for about 60% of the total insulin secretion after meals, and plays an important role in blood sugar regulation. GLP-1 and glucose-dependent insulinotropic polypeptide (GIP) are two major incretins. Among them, the secretion of the former is significantly reduced in patients with type 2 diabetes (even those with impaired glucose tolerance), so that GLP-1 has become an important therapeutic target. Studies on the physiological effects of GLP-1 have shown that GLP-1 can not only enhance insulin secretion of β-cells, but also reduce glucagon secretion by acting on α-cells, thereby reducing glycogen output; and GLP-1 acts on the central nervous system and stomach to suppress appetite and slow down Gastric emptying, thereby reducing β-cell load, etc. However, since GLP-1 is rapidly degraded by dipeptidyl peptidase 4 (DPP-4) in vivo, its duration of action is limited. Therefore, the current GLP-1-based methods to improve blood sugar control include exogenous drugs that mimic the effect of GLP-1 and prolong the activity of endogenous GLP-1. GLP-1 receptor agonists play a hypoglycemic effect based on this.

After GLP-1(7-36) amide, which serves as the main active form of GLP-1, enters blood circulation, dipeptidyl peptidase IV (DPP-IV) on the blood and cell membrane will rapidly cleave GLP-1(7-36) amide into inactive GLP-1(9-36), with the half-life being only 1-2 min, so that GLP-1(7-36) amide is not suitable for long-term treatment of type 2 diabetes (T2DM). Further, scientific research has carried out corresponding transformation and modification on the structure of GLP-1 to increase its half-life, so as to prolong the biological effect in vivo. Diabetes is a chronic disease characterized by hyperglycemia due to insufficient insulin secretion (relative or absolute) or insulin action dysfunction. Type 2 diabetes is a progressive disease. The patient's condition deteriorates over time. It is difficult to control blood sugar well for a long time even with conventional drug treatment. Regardless of metformin, sulfonylureas, or insulin monotherapy, it is difficult to achieve the goal of glycosylated hemoglobin (HbA1c) continuously. To explore the reason, it is related to the progressive decline of β-cell function. GLP-1 can also increase insulin synthesis in vivo, promote β-cell proliferation and differentiation, and inhibit β-cell apoptosis. These characteristics may help to reverse or even prevent diabetes.

GLP-1R agonists known in the prior art for the treatment or prevention of diabetes are generally macromolecular polypeptides, such as lixisenatide, liraglutide, and exenatide, which are difficult to synthesize and prepare and are higher in cost; it is needed to inject them to administrate, which leads to poor patient compliance, and the development of small molecule GLP-1R agonists will improve patient compliance and medication convenience, and reduce drug costs, so that the small molecule GLP-1R agonists have broad clinical market prospects. Therefore, it is of great research significance and commercial value to develop a class of GLP-1R agonists based on small molecular structure.

The chemical structure of anisomycin is as follows:

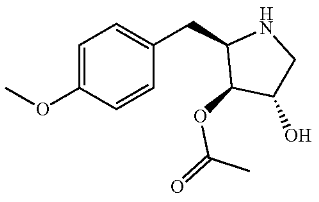 [SMILES: COc1ccc(C[C@H]2NC[C@H](O)[C@H]2OC(C)=O)cc1]

CAS number: 22862-76-6, molecular weight: 265.30, chemical name: (2R,3S,4S)-2-[(4-methoxyphenyl)methyl]-3,4-pyrrolidinediol 3-acetate methyl ester, which is a pyrrolidine antibiotic separated from *Streptomyces griseus*. Anisomycin is a protein synthesis inhibitor, which has a good inhibitory effect on some fungi and pathogens, has been successfully used clinically to treat vaginitis caused by trichomonas and dysentery caused by amebic protozoa, etc., and is also widely used to control fungal diseases of plants. Studies have found that anisomycin can significantly inhibit the reactivity of T lymphocytes, with no cytotoxicity found, and can inhibit the rejection reaction of mouse skin transplantation, with its immunosuppressive effect higher than that of the immunosuppressive drug cyclosporin A, and lower toxicity. Therefore, it may be tried for the development of immunosuppressive drugs to treat autoimmune diseases. In addition, anisomycin can activate p38 MAPK and JNKs, and p38 and JNK signaling pathways are involved in various cellular activities, such as cell proliferation and differentiation, apoptosis, etc., suggesting that anisomycin has potential anti-tumor activity and can be used in the development of anti-tumor drugs. The inventor has unexpectedly found that anisomycin has the effect of stimulating GLP-1R, can be used in drugs as the GLP-1R agonist to promote insulin secretion, lower blood sugar, treat diabetes, and has other effects as the GLP-1R agonist. It has not been reported previously that anisomycin and derivatives thereof can stimulate GLP-1R.

SUMMARY

In order to overcome the disadvantages of synthesis and application of GLP-1R receptor agonists in the prior art because they are all macromolecular polypeptides, the present invention provides use of anisomycin in preparation of a GLP-1R agonist.

The object of the present invention is achieved by the following technical solution:

an anisomycin derivative represented by general formula (I) or pharmaceutically acceptable salts, solvates and stereoisomers thereof, (I)

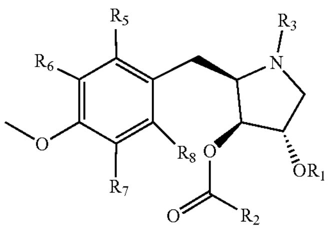

where $R_1$ is selected from hydrogen, optionally substituted C1-6 alkyl, and —C(O)$R_4$; $R_2$ is selected from hydrogen, optionally substituted C1-6 alkyl, optionally substituted C1-6 alkoxy, and —NH—$R_4$; $R_3$ is selected from hydrogen, optionally substituted C1-6 alkyl, optionally substituted C1-6 alkyl, optionally substituted C6-12 aryl, optionally substituted heteroaryl, and —C(O)$R_4$; $R_4$ is selected from H, optionally substituted C1-6 alkyl, and optionally substituted C1-6 alkoxy; $R_5$, $R_6$, $R_7$, and $R_8$ are independently selected from halogen atoms, nitro, —COO$R_9$, CONH$R_9$, optionally substituted C1-6 alkyl, and optionally substituted C1-6 alkoxy; and $R_9$ is selected from H, and optionally substituted C1-6 alkyl on condition that the compound of general formula (I) is not anisomycin.

Preferably, the anisomycin derivative provided by the present invention is the following compound 1 and compound 2:

1

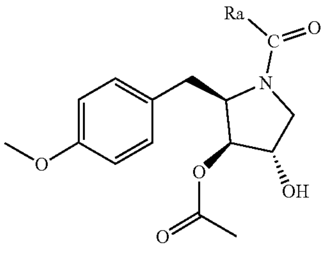

-continued

2

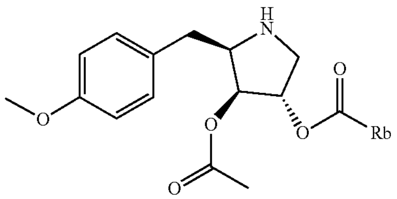

where Ra and Rb are independently selected from optionally substituted C1-6 alkyl, C1-6 alkoxy, and C6-20 aryl.

The C1-6 alkyl is selected from methyl, ethyl, propyl, and butyl; the C6-20 aryl is selected from phenyl, naphthyl, and anthracenyl; the optional substitution means that any H atom is substituted by hydroxyl, a halogen atom, nitro, C1-4 alkyl, and C1-4 alkoxy.

A GLP-1R agonist, including at least one of anisomycin, anisomycin derivatives represented by general formula (I) or pharmaceutically acceptable salts, solvates, and stereoisomers thereof as active ingredients.

The derivative includes products obtained from some group substitutions or reactions by taking anisomycin as the parent, such as substances substituted by halogen atoms, alkyl, alkenyl, alkynyl, alkoxy, hydroxyl, aryl or heteroaryl, or products obtained by reacting with other substances with reactive functional groups, such as products of esterification, etherification, amidation, transesterification, etc.; or salts thereof, such as quaternary ammonium salts; or deuterated derivatives thereof, where deuterated hydrogen is not particularly specified, and is preferably active hydrogen, such as hydrogen on amino or hydrogen on hydroxyl.

Use of at least one of anisomycin, anisomycin derivatives represented by general formula (I) or pharmaceutically acceptable salts, solvates, and stereoisomers thereof in preparation of the GLP-1R agonist.

Further, the present invention provides use of at least one of anisomycin, anisomycin derivatives represented by general formula (I) or pharmaceutically acceptable salts, solvates, and stereoisomers thereof in preparation of drugs to treat GLP-1R-mediated diseases.

The GLP-1R-mediated diseases include, but not limited to, obesity, diabetes, weight loss, systolic blood pressure reduction, epilepsy, cerebral ischemic disease, Alzheimer's disease, fatty liver, dyslipidemia, and neuroprotection.

The present invention further provides use of at least one of anisomycin, anisomycin derivatives represented by general formula (I) or pharmaceutically acceptable salts, solvates, and stereoisomers thereof in preparation of drugs to treat diabetes, dyslipidemia, metabolic syndrome, hyperinsulinemia, nocturnal hypoglycemia, obesity, weight loss, systolic blood pressure reduction, Alzheimer's disease, fatty liver and neuroprotection.

Preferably, the diabetes is selected from type 2 diabetes.

The inventor has unexpectedly found that anisomycin and the derivative thereof have the function of GLP-1R agonists, and can be used as drugs for treating diabetes. Insulin secretion is stimulated in a glucose concentration-dependent manner through the GLP-1 receptor (GLP-1R), that is, the anisomycin and the derivative thereof will only play a role in promoting insulin secretion at a certain concentration of blood sugar, and will not play a role at a lower blood sugar concentration. Therefore, while treating diabetes, hypoglycemia can also be avoided, which is the benefit of the GLP-1R agonist as a drug for treating diabetes compared with conventional drugs.

Further, the present invention provides the GLP-1R agonist taking at least one of anisomycin, anisomycin derivatives represented by general formula (I) or pharmaceutically acceptable salts, solvates, and stereoisomers thereof as active ingredients, with the dosage of 0.5-50 mg/kg, and preferably, with the dosage of 5-30 mg/kg.

The present invention further provides a pharmaceutical composition with GLP-1R agonistic activity, including at least one of anisomycin, anisomycin derivatives represented by general formula (I) or pharmaceutically acceptable salts, solvates, and stereoisomers thereof as active ingredients.

Further, the present invention provides a pharmaceutical composition for treating or preventing diabetes, including at least one of anisomycin, anisomycin derivatives represented by general formula (I) or pharmaceutically acceptable salts, solvates, and stereoisomers thereof as active ingredients.

The pharmaceutical composition can further include metformin, SGLT-2 inhibitors, etc. and excipients.

The pharmaceutical composition is used in dosage forms well known in the art, such as tablets, capsules, and injections.

In particular, the present invention provides a method for reducing glucose levels in blood, which specifically includes administering an effective dosage of at least one of anisomycin or derivatives, salts, and solvates thereof.

The GLP-1R agonist effect of the anisomycin and derivatives thereof in the present invention is dependent on blood sugar concentration. Therefore, the above method of the present invention can not only treat or prevent diabetes, but also effectively reduce the occurrence of hypoglycemia.

DETAILED DESCRIPTION

Preparation Example

Figure 1:
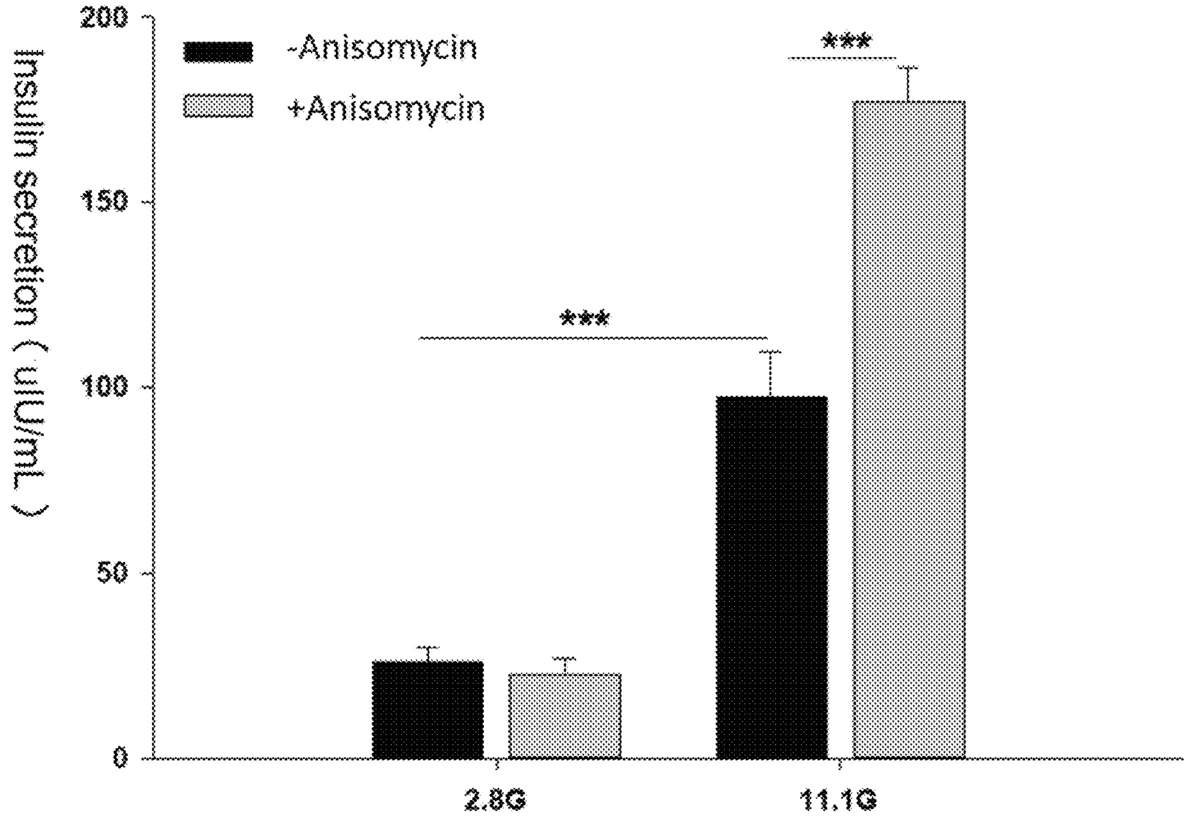
FIG. 1 shows the effect of anisomycin on insulin secretion in rats.

By taking anisomycin as raw material, different anisomycin derivatives are obtained according to the following synthetic routes.

| Compound 1 | Ra |
|---|---|
| 1-1 | —Ph |
| 1-2 | —$C_2H_5$ |
| 1-3 | -4-Cl—Ph |
| Compound 2 | Rb |
| 2-1 | —Ph |
| 2-2 | —$C_2H_5$ |

-continued

| | |
|---|---|
| 2-3 | —$C_3H_7$ |

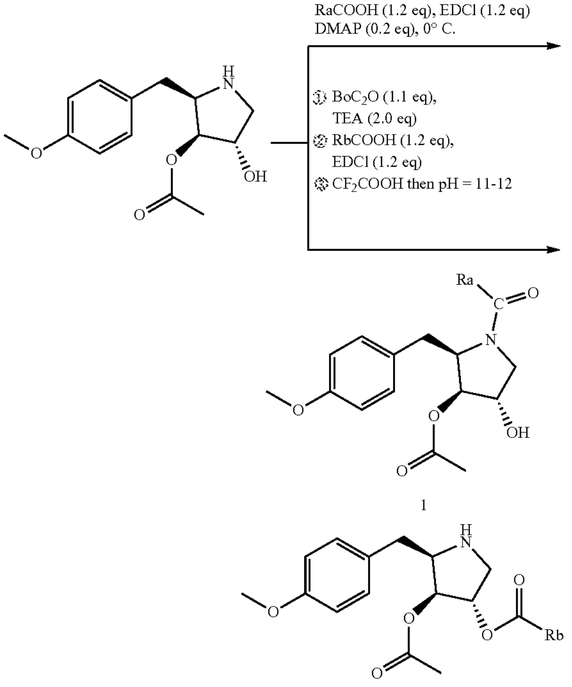

1

2

Example 1

Materials and methods used in the present invention are described below.

1.1 Experimental Animals

Male Wistar rats, with the body weight of 180-250 g, are purchased from the Experimental Animal Center of Shanxi Provincial People's Hospital, where the feeding temperature is 20-22° C., and standard food and drinking water for rodents are equipped. All operating flows meet management and instruction manuals for experimental animals of Shanxi Medical University.

1.2 Main Drugs and Reagents

| | |
|---|---|
| Anisomycin | MCE |
| Glucose | Beijing Solarbio Science & Technology Co., Ltd. |
| DispaseII | AMRESCO |
| TEA | Sigma-Aldrich (Shanghai) Trading Co., Ltd. |
| Histopaque-1077 | Sigma-Aldrich (Shanghai) Trading Co., Ltd. |
| Albumin bovine serum (BSA) | Beijing Solarbio Science & Technology Co., Ltd. |
| RPMI 1640 culture medium | HYCLONE |
| Collagenase P | Roche Pharma(Schweiz) Ltd. |
| Fura 2-AM | DOJINDO |
| Fetal calf serum (FBS) | Thermo Fisher |
| Hanks buffer solution (HBSS) | BOSTER Biological Technology Co. Ltd. |
| Analytically pure NaCl | BBI Life Sciences Corporation |
| Analytically pure KCl | BBI Life Sciences Corporation |
| $NaHCO_3$ | BBI Life Sciences Corporation |
| HEPES | Beijing Solarbio Science & Technology Co., Ltd. |
| $CaCl_2$ | BBI Life Sciences Corporation |
| Analytically pure $MgCl_2$ | BBI Life Sciences Corporation |
| $KH_2PO_4$ | BBI Life Sciences Corporation |

-continued

| | |
|---|---|
| 100* mycillin mixed solution | Beijing Solarbio Science & Technology Co., Ltd. |
| DMSO | Beijing Solarbio Science & Technology Co., Ltd. |
| $MgSO_4$ | BBI Life Sciences Corporation |

2. Main Experimental Instruments

| | |
|---|---|
| Cell incubator | Eppendorf |
| Thermostatic oscillator | Changzhou Guohua Electric Appliance Company Limited |
| Pressure steam sterilizer | Taiyuan Xingyu Scientific and Educational Instrument and Equipment Manufacturing Co., Ltd. |
| Clean bench | Shanghai Zhicheng Analytical Instrument Manufacturing Co., Ltd. |
| Medical refrigerator-freezer | AUCMA |
| Full automatic snowflake ice machine | Changshu Xueke Electric Appliance Company Limited |
| Acidimeter | OHAUS |
| Digital rotating speed peristaltic pump | Baoding Chuangrui Pump Co. Ltd. |
| Inverted microscope | Olympus IX51 |
| VORTEX vortex mixer | Haimen Qilinbeier Instrument Co. Ltd. |

3. Isolation and Culture of Tissues of Pancreas Islets of the Rats are Conventional Operations for Those Skilled in the Art.

4. Data Processing and Statistics

Data involved are processed with SigmaPlot12.5 software and are represented by Mean±SEM. Statistic analysis is performed with Student's t-test, one-way ANOVA or paired t-test. In a case where $p<0.05$, it is of statistical significance.

Specific Operations 5.1 Influence of Anisomycin on Secretion of Rat Insulin

Preparation before experiments: 1) there were four groups of experiments, and Ep (Eppendorf) tubes were numbered (7 for each group); 2) a KRBH solution was prepared and was placed in an incubator for inculcation for 30 min, and the pH value was regulated with NaOH to 7.4; and 3) a sample to be tested was prepared from a 2.8 mmol/L glucose solution (2.8G), 2.8G+10 μM anisomycin, a 11.1 mmol/L glucose solution (11.1G) and 11.1G+10 μM anisomycin.

Experimental steps: 1) 500 μL of 2.8G was added into each Ep tube, 5 pancreas islets (uniform in size and smooth in edge) were picked under a stereomicroscope and were placed in the Ep tube, and the Ep tube was placed in the incubator for incubation for 30 min; 2) a supernate was sucked out and abandoned with a pipette, where the pancreas islets were not sucked out, and then 500 μL of 2.8G, 2.8G+10 μM anisomycin, 11.1G and 11.1G+10 μM anisomycin were added into each group in sequence, and the Ep tube was placed in the incubator for incubation for 30 min; and 3) the supernate was sucked out with the pipette to the Ep tube marked in advance, the mixture was uniformly mixed, and the Ep tube was sealed and preserved at 4° C. The content of insulin in each group is detected by insulin radioimmunoassay.

The experimental results are shown in FIG. 1, with the influence of anisomycin on secretion of rat insulin, where +anisomycin represents addition of a certain amount of anisomycin, and +anisomycin in the following figures represents the same meaning. The pancreas islets of the rats are respectively incubated at low glucose concentration (2.8G) and high glucose concentration (11.1G) with anisomycin (10 μM). n=7. ***$P<0.001$. At the basic glucose concentration (2.8G), anisomycin does not have the effect of promoting insulin secretion; at the high glucose concentration (11.1G), anisomycin has the significant effect of promoting insulin secretion. It indicates that anisomycin promotes insulin secretion at high glucose concentration.

5.2 Influence of Anisomycin with Different Dosages on Secretion of Rat Insulin

Preparation before experiments: 1) there were four groups of experiments, and Ep (Eppendorf) tubes were numbered (7 for each group); and 2) a sample to be tested was prepared from a 2.8 mmol/L glucose solution (2.8G), a 11.1 mmol/L glucose solution (11.1G), 11.1G+0.1 μM anisomycin, 11.1G+1 μM anisomycin, and 11.1G+10 μM anisomycin.

Experimental steps: 1) pre-incubation was performed at 2.8G for 30 min; 2) the Ep tube was taken out, the supernate was abandoned, and then 500 μL of 11.1G, 11.1G+0.1 μM anisomycin, 11.1G+1 μM anisomycin and 11.1G+10 μM anisomycin were added into each group in sequence, and the Ep tube was placed in the incubator for incubation for 30 min; and 3) the supernate was sucked out with the pipette to the Ep tube marked in advance, the mixture was uniformly mixed, and the Ep tube was sealed and preserved at 4° C. The content of insulin in each group is detected by insulin radioimmunoassay.

Figure 2:
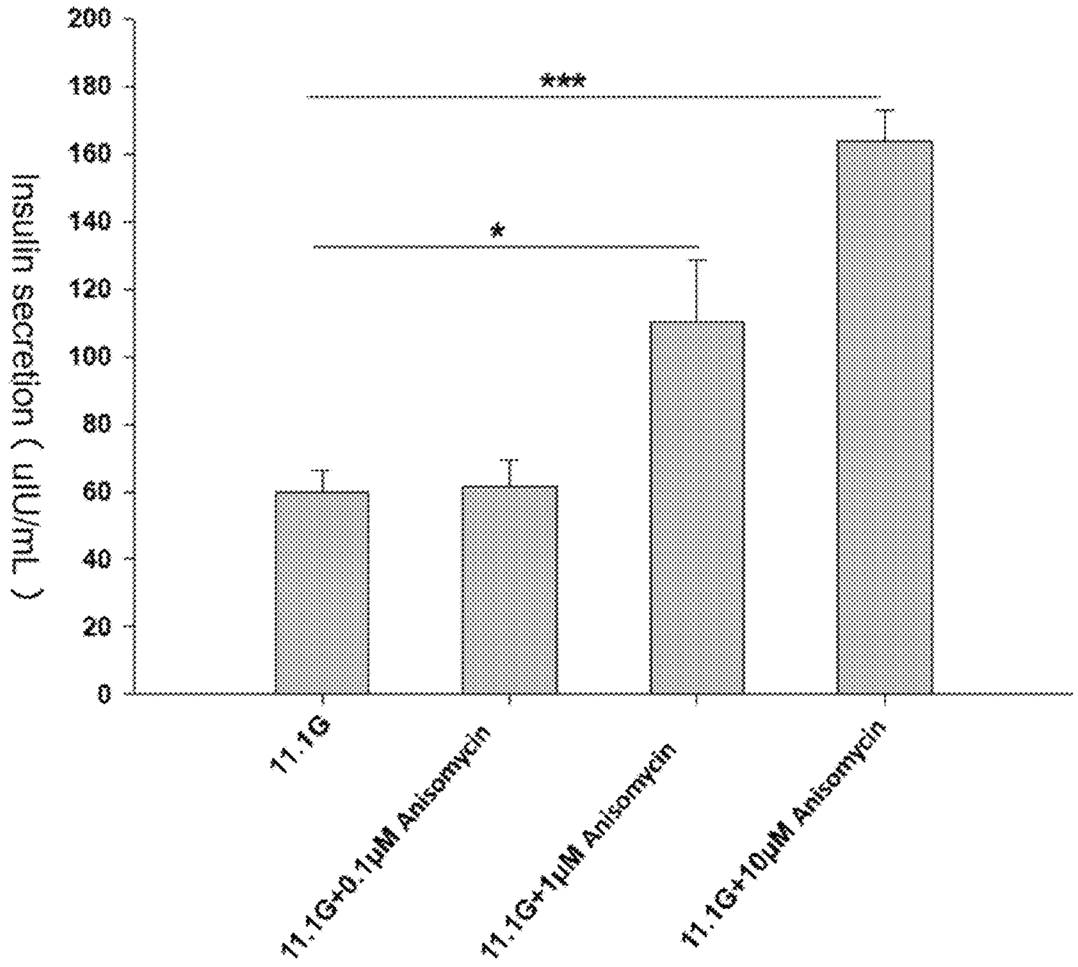
FIG. 2 shows the effects of different dosages of anisomycin on insulin secretion in rats.

The experimental results are shown in FIG. 2, with influence of anisomycin with different dosages on secretion of rat insulin. At the 11.1 mmol/L glucose concentration (11.1G), anisomycin with different concentrations (0.1 μM, 1 μM and 10 μM) are used to incubator the pancreas islets of the rats. n=7. *$P<0.05$; ***$P<0.001$. Compared with independent administration of 11.1 mmol/L glucose (11.1G), with increase of the concentration of anisomycin, the effect of anisomycin promoting insulin secretion is gradually enhanced, and when the concentration of anisomycin is 1 μM and 10 μM, anisomycin has the significant effect of promoting insulin secretion. Therefore, anisomycin has the concentration-dependent effect of promoting insulin secretion at the high glucose concentration (11.1G).

5.3 Influence of Anisomycin at Different Glucose Concentrations on Insulin Secretion of the Pancreas Islets of the Rats Preparation before experiments: 1) there were three groups of experiments, and Ep tubes were numbered (7 for each group); and 2) a sample to be tested was prepared from a 2.8 mmol/L glucose solution (2.8G), 2.8G+10 μM anisomycin, a 11.1 mmol/L glucose solution (11.1G), 11.1G+10 μM anisomycin, a 16.7 mmol/L glucose solution (16.7G) and 16.7G+10 μM anisomycin.

Experimental steps: 1) pre-incubation was performed at 2.8G for 30 min; 2) the Ep tube was taken out, the supernate was abandoned, and then 500 μL of 2.8G, 11.1G and 16.7G were added into each group in sequence, and the Ep tube was placed in the incubator for incubation for 30 min; 3) the supernate was sucked out with the pipette to the Ep tube marked in advance, the mixture was uniformly mixed, and the Ep tube was sealed and preserved at 4° C., and 500 μL of 2.8G+10 μM anisomycin, 11.1G+10 μM anisomycin and 16.7G+10 μM anisomycin were added in sequence according to the dosing sequence in the previous round, and the Ep tube was placed in the incubator for incubation for 30 min; and 4) the Ep tube was taken out, the supernate was sucked out to the numbered Ep tubE, the mixture was mixed, and the Ep tube was sealed and preserved at 4° C. The content of insulin in each group is detected by insulin (INS) radioimmunoassay.

Figure 3:
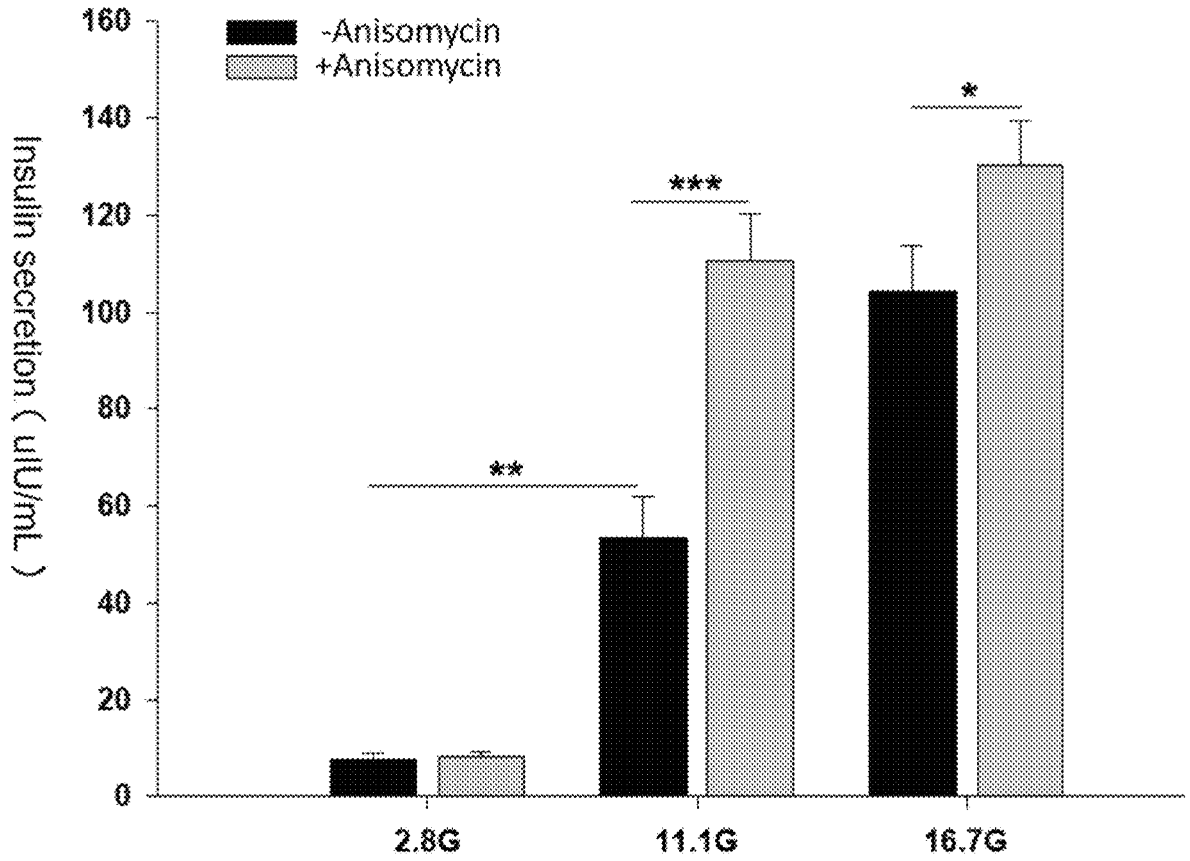
FIG. 3 shows the effects of anisomycin on insulin secretion in rats under different glucose concentrations.

The experimental results are shown in FIG. 3, with the influence of anisomycin at different glucose concentrations on secretion of rat insulin. At the 2.8 mmol/L glucose concentration (2.8G), the 11.1 mmol/L glucose concentration (11.1G) and the 16.7 mmol/L glucose concentration (16.7G), the pancreas islets of the rats are incubated with 10 μm anisomycin. n=7, *p<0.5, p<0.01, *p<0.001. It can be seen that at the basic glucose concentration (2.8G), anisomycin does not have the effect of promoting secretion of insulin; at the concentration of the 11.1 mmol/L glucose solution (11.1G), anisomycin has the significant effect of promoting secretion of insulin; with increase of glucose concentration, at the concentration of the 16.7 mmol/L glucose solution (16.7G), anisomycin can still promote secretion of insulin with significant difference. Therefore, anisomycin has the glucose concentration-dependent effect of promoting insulin secretion. It can be illustrated that since anisomycin has the blood sugar concentration dependence, it still can avoid hypoglycemia when being used to treat or prevent diabetes.

Example 2 Effect of GLP-1 on Regulating Secretion of Rat Insulin by Ranisomycin 1.1 Test Reagents

| | |
|---|---|
| Exendin (9-30) | MCE |
| Bg1II, NotI, Nsil, HindIII | Fermentas |
| Tween-20 | Beijing Solarbio Science & Technology Co., Ltd. |
| Medium extraction kit | Hangzhou Axygen Biotechnology Co., Ltd. |
| DNA gel extraction kit | Tiangen Biotechnology (Beijing) Co., Ltd. |
| M5 Prestained Plus Protein Ladder | Mei5 Biotechnology Co., Ltd |
| DNA ligase | Fermentas |
| Biodlight ™ ECL Chemiluminescent HRP Substrate (High Sensitivity) | Bioworld |
| BamHI, EcoRI, NheI, DNA marker | Fermentas |
| Smal, XhoL, EcoRV | Millipore |
| DNA polymerase | Sangong Biotech |
| High purity plasmid extraction mini kit | Tiangen Biotechnology (Beijing) Co., Ltd. |
| Tryptone and yeast extract | Theromo Fisher |
| Dialytic *E. coli* cell-free recombinant protein expression kit | Hangzhou Jinao Biotechnology Co., Ltd. |
| Dialytic TOB cell-free recombinant protein expression kit | Hangzhou Jinao Biotechnology Co., Ltd. |
| Dialytic Yeast cell-free recombinant protein expression kit | Hangzhou Jinao Biotechnology Co., Ltd. |
| ClonExpress ® Entry One Step Cloning Kit | Vazyme Biotech Co., Ltd |

1.2 Main Experimental Instruments

| | |
|---|---|
| PCR meter | Bio-rad |
| Gel imaging system | Bio-rad |
| Western blot vertical electrophoresis system | Bio-rad |
| Western blot half-dry transmembrane system | Bio-rad |
| Octet RE96E molecular interaction analyzer | Fortebio |
| Balance | Shanghai Tianmei Scientific Instrument Co., Ltd. |
| Pipette | Eppendorf Research plus set |
| SSA chip | Fortebio |
| Acidimeter | OHAUS |
| Digital rotating speed peristaltic pump | Baoding Chuangrui Pump Co. Ltd. |
| VORTEX vortex mixer | Haimen Qilinbeier Instrument Co. Ltd. |

2.1 Effect of GLP-1 on Regulating Insulin Secretion by Ranisomycin

Preparation before experiments: 1) there were four groups of experiments, and Ep tubes were numbered (7 for each group); and 2) a sample to be tested was prepared from a 2.8 mmol/L glucose solution (2.8G), a 11.1 mmol/L glucose solution (11.1G), 11.1G+100 nM Exendin(9-39), 11.1G+10 μM ranisomycin, and 11.1G+100 nM Exendin(9-39)+10 μM ranisomycin.

Experimental steps: 1) pre-incubation was performed at 2.8G for 30 min; 2) the Ep tube was taken out, the supernate was abandoned, and then 500 μL of 11.1G, 11.1G+100 nM Exendin(9-39), 11.1G+10 μM anisomycin and 11.1G+100 nM Exendin(9-39)+10 μM anisomycin were added into each group in sequence, and the Ep tube was placed in the incubator for incubation for 30 min; and 3) the supernate was sucked out with the pipette to the Ep tube marked in advance, the mixture was uniformly mixed, and the Ep tube was sealed and preserved at 4° C. The content of insulin in each group is detected by insulin radioimmunoassay.

Figure 4:
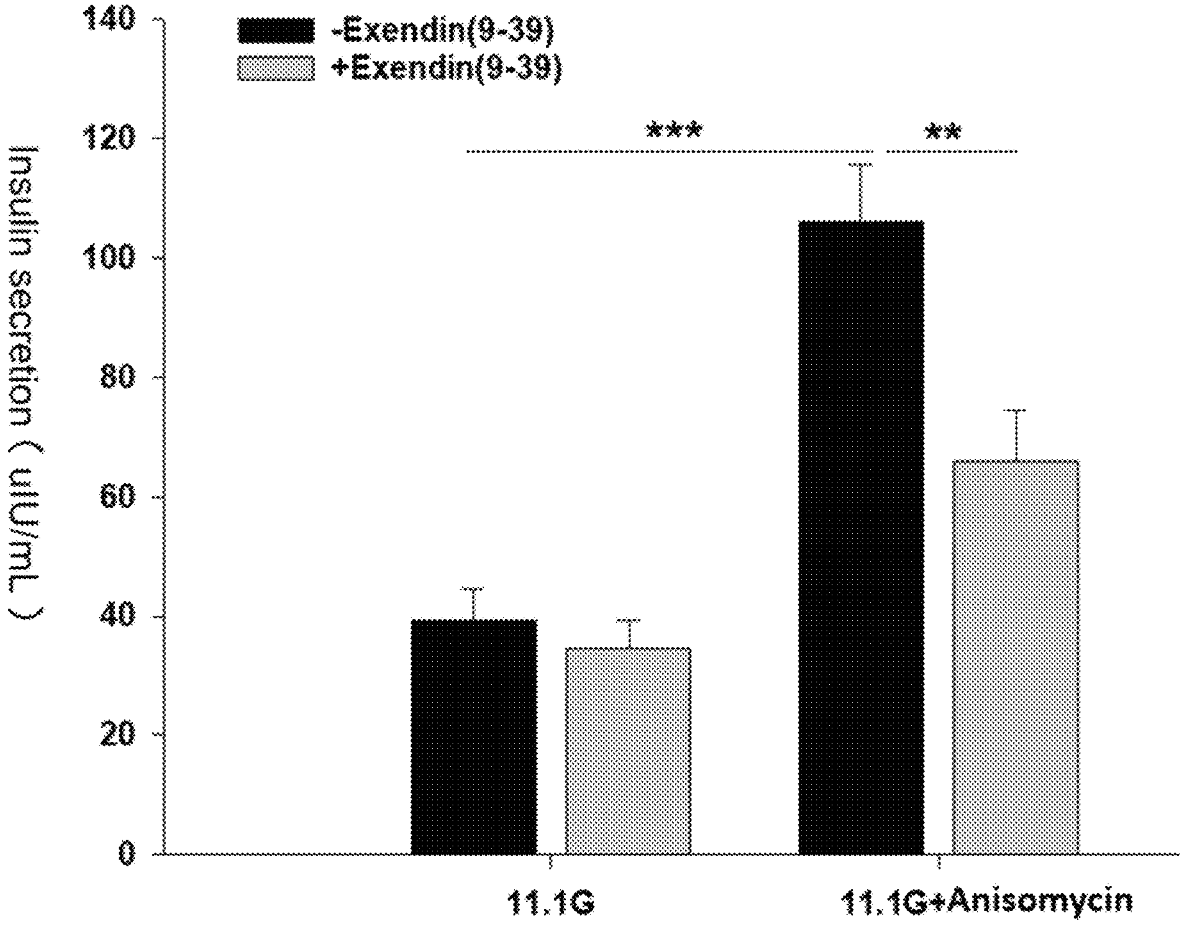
FIG. 4 shows the effect of anisomycin on insulin secretion in rats in the presence or absence of a GLP-1R blocker Exendin (9-39).

The experimental results are shown in FIG. 4, with the effect of GLP-1 on regulating insulin secretion by ranisomycin. At the 11.1 mmol/L glucose concentration (11.1G), 10 μm anisomycin and 100 nM Exendin(9-39) are used to incubator the pancreas islets of the rats. n=7, p<0.01, *p<0.001. Exendin(9-39) is a specifically competitive GLP-1R agonist, which can block the agonistic action of the GLP-1R agonist to GLP-1R. At the concentration of the 11.1 mmol/L glucose solution (11.1G), Exendin(9-39) blocks the effect of anisomycin promoting insulin secretion, indicating that the effect of anisomycin promoting insulin secretion is related to the agonistic GLP-1R.

2.2 ForteBio Octet Molecular Interaction to Detect the Affinity of Anisomycin and GLP-1R Expression of a cell-free GLP-1R protein: 1) construction of a rat GLP-1R vector: a sequence fragment of rat GLP-1R was obtained by a PCR amplification technique, the GLP-1R rat gene fragment was recovered with an agarose gel, a target gene GLP-1R was cloned to a vector pEX-3, pEX-3 was di-cleaved with EcoRI and BamHI, and was subjected to electrophoresis to recover the vector pEX-3; the amplified fragment are recombined and cloned to the pEX-3 vector by means of ClonExpress® Entry One Step Cloning Kit; the recombinant joint product was converted into a competent cell, clonal colonies were picked and a small amount of the clonal colonies were extracted to obtain plasmids, the plasmids were subjected to di-cleaved identification with EcoRI and BamHI, the plasmids were subjected to electrophoresis, and positive clones were picked; a large amount of recombinant plasmids subjected to sequencing verification were extracted, a bacteria solution corresponding to the positive clones was sequenced, and the residual bacteria solution was preserved with glycerinum; the sequencing result was compared with the target gene sequence, after corrected verification, it was inoculated to an LB culture medium with a glycerinum bacteria solution, and a large amount of plasmids were extracted to obtain an enough amount of recombinant plasmids; and 2) expression of the cell-free GLP-1R protein: the target gene was amplified with high fidelity DNA polymerase G-POL-001 or Z2 ultra fidelity DNA polymerase G-POL-002 purchased from Hangzhou Jinao Biotechnology Co. Ltd. To improve the success rate of protein expression, an *E. coli* dialytic cell-free protein expression system, a TOB dialytic cell-free protein expression system and a Yeast dialytic cell-free protein expression system were used for expression, and finally, the expression result was observed with SDS-PAGE.

GLP-IR protein purification and concentration: 1) a His-trap column was used to purify a target protein; and 2) a purified sample was acquired, and SDS-PACE was performed to observe a purification result.

Experimental steps of ForteBio Octet molecular interaction: 1) biotinylation treatment was performed on the GLP-1R protein, a proper amount of a biotinylation reagent was added for a water bath reaction at 30° C. for 2 h, residual biotins were removed by a gravity desalting column after the reaction, and the mixture was eluted with PBS for SSA chip curing; 2) the compound was dissolved with DMSO, was diluted 100 times after being fully dissolved, and was then diluted with 1% DMSO+PBST to 21.2 μM, 42.4 μM, 84.8 μM and 169.5 μM, 339 μM, respectively for follow-up detection; 3) the above samples and reagents were added into a sample board in sequence; and 4) a program was set for detection.

Figure 5:
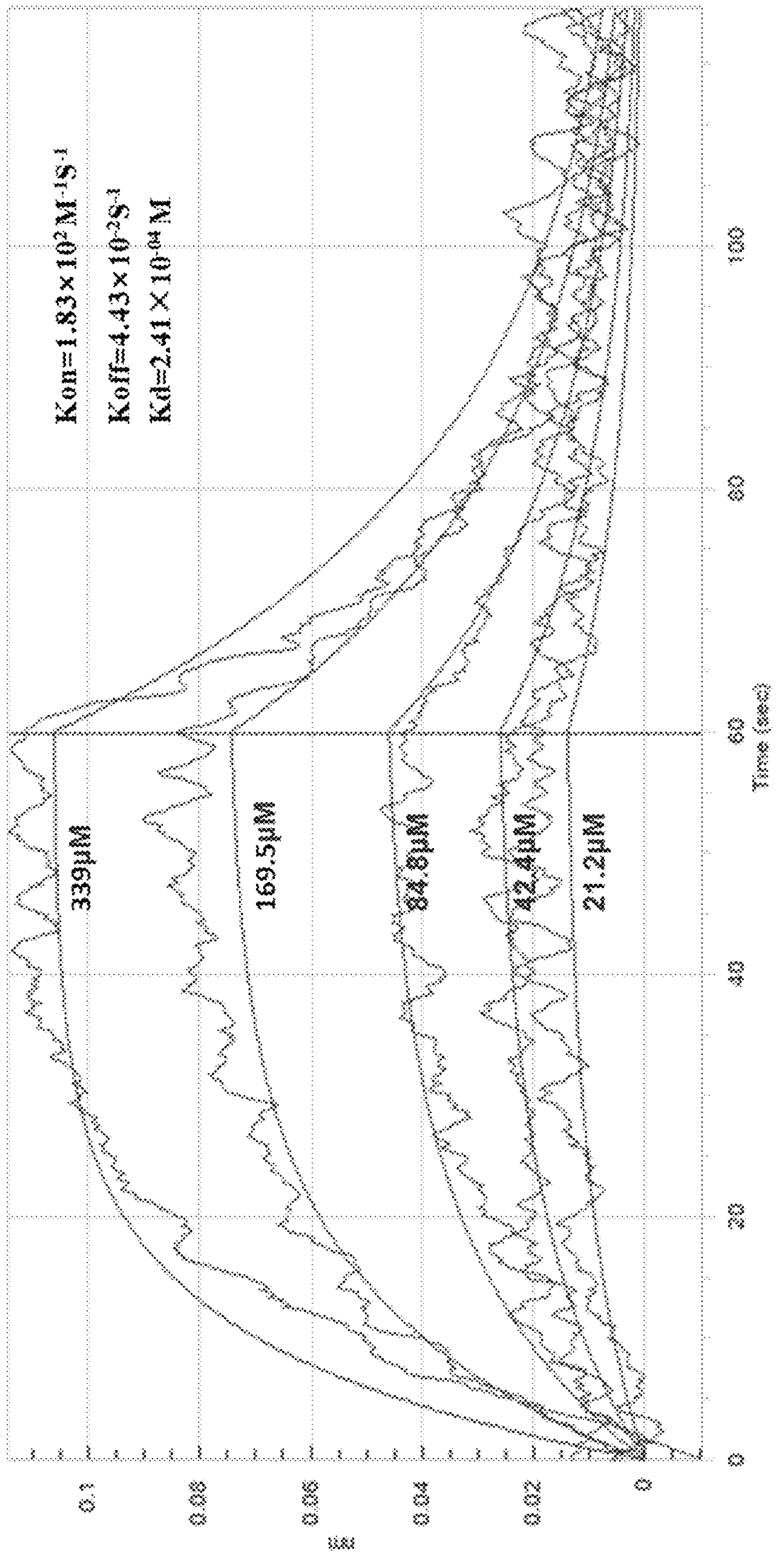
FIG. 5 shows ForteBio Octet molecular interaction to detect the affinity of anisomycin and GLP-1R.

$K_{on}$ is the association rate constant, which reflects the speed of intermolecular binding; $K_{off}$ is the dissociation rate constant, which reflects the speed of intermolecular dissociation; Kd is the dissociation constant, which reflects the amplitude of affinity of the compound to the target, where the less the value is, the higher the affinity is. $Kd=K_{off}/K_{on}$. For small molecules (<2 kDa), the value Kd is $10^{-4}$-$10^{-7}$M, which shows higher affinity. The results are shown in FIG. 5. The ForteBio Octet intermolecular interaction result shows that Kd of anisomycin is equal to $2.41\times10^{-04}$M, which shows that anisomycin has higher affinity with GLP-1R.

It can be seen from the data in the examples 1 and 2 that anisomycin can effectively promote insulin secretion at higher blood glucose concentration, with certain blood glucose concentration dependence. Moreover, under the action of the GLP-1R agonist, the effect of promoting insulin secretion is reduced or disappears, indicating that GLP-1R mediates the effect of anisomycin promoting insulin secretion. According to the present invention, through ForteBio Octet molecular interaction detection, it is verified that anisomycin and GLP-1R have apparent interaction and higher affinity. The above data can fully show that anisomycin is an effective small molecule GLP-1R agonist.

Example 3 Influence of Anisomycin on Blood Glucose of C57BL/6 Mice

1. Materials and Methods 1.1 Experimental Animals

Male C57BL/6 mice, with the body weight of 18-22 g, are purchased from the Experimental Animal Center of Shanxi Provincial People's Hospital, where the feeding temperature is 20-22° C., and standard food and drinking water for rodents are equipped. All operating flows meet management and instruction manuals for experimental animals of Shanxi Medical University.

1.2 Main Drugs and Reagents

| | |
|---|---|
| Anisomycin | MCE |
| Glucose | Beijing Solarbio Science & Technology Co., Ltd. |
| DMSO | Beijing Solarbio Science & Technology Co., Ltd. |
| PEG-200 | Beijing Solarbio Science & Technology Co., Ltd. |

1.3 Main Experimental Instruments

| | |
|---|---|
| Animal balance | Shanghai Fixal Tools Co. Ltd. |
| FreeStyle glucometer and blood glucose test strip | Abbott Diabetes Care Ltd. |

-continued

| | |
|---|---|
| Low-temperature Ultra-high speed centrifugal machine | Eppendorf |
| Full automatic snowflake ice machine | Changshu Xueke Electric Appliance Company Limited |
| Digital rotating speed peristaltic pump | Baoding Chuangrui Pump Co. Ltd. |
| Micro vortex mixer | Shanghai Huxi Analytic Instrument Co., Ltd. |
| Magnetic stirrer | Shanghai Silei Instrument Co., Ltd. |

1.4 Data Processing and Statistics

Data involved are processed with SigmaPlot12.5 and are represented by Mean±SEM. Statistic analysis is performed with Student's t-test, one-way ANOVA or paired t-test. In a case where $P<0.05$, it is of statistical significance.

2 Experimental Results 2.1 Oral Glucose Tolerance Test (OGTT)

Drug preparation: anisomycin was dissolved in DMSO, then PEG200 was added, and finally, the mixture was diluted with normal saline (DMSO:PEG200:normal saline=1:4:5).

21 SPF level 6-weeks old C57BL/6 mice were fed adaptively for 1 week and were randomly divided into the following three groups: control group: a solvent (DMSO: PEG200:normal saline=1:4:5) was intraperitoneally injected; 5 mg/kg anisomycin group: a 5 mg/kg anisomycin solution was intraperitoneally injected; and 15 mg/kg anisomycin group: a 15 mg/kg anisomycin solution was intraperitoneally injected, where the administration volume was 0.1 ml/10 g, each group had 7 mice, and the mice drank water and ingested food freely. Before experiments, the mice in each group were subjected to fasting rather than water deprivation for 12 h, gastric irrigation of a 40% glucose solution (2 mg/kg) was performed for each group of mice after administration, blood was sampled from caudal veins in 0 min, 15 min, 30 min, 60 min, 90 min and 120 min after gastric irrigation, blood glucose levels were measured with a glucometer, and the areas under the curve (AUC) of blood glucose were calculated.

Figure 6A:
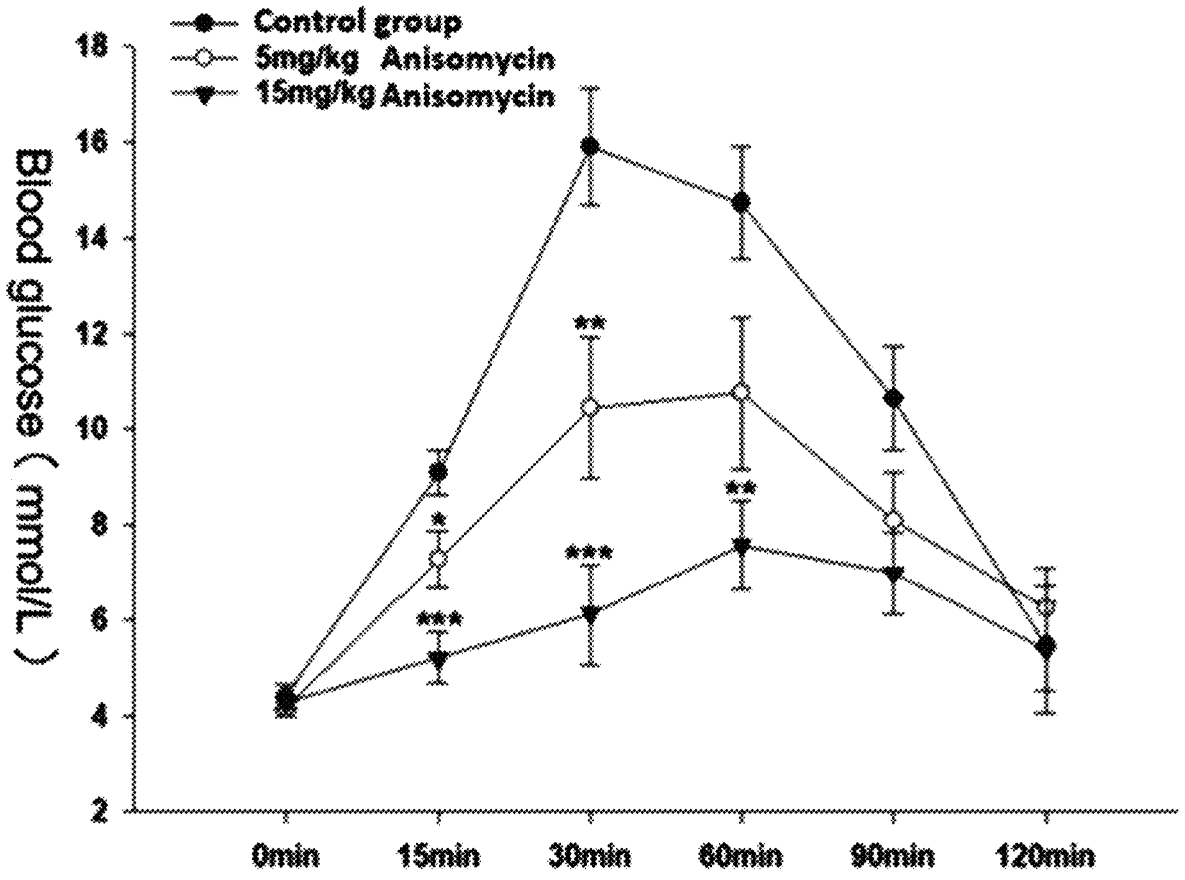
FIG. 6A shows a curve of blood glucose change over time in an oral glucose tolerance test.
Figure 6B:
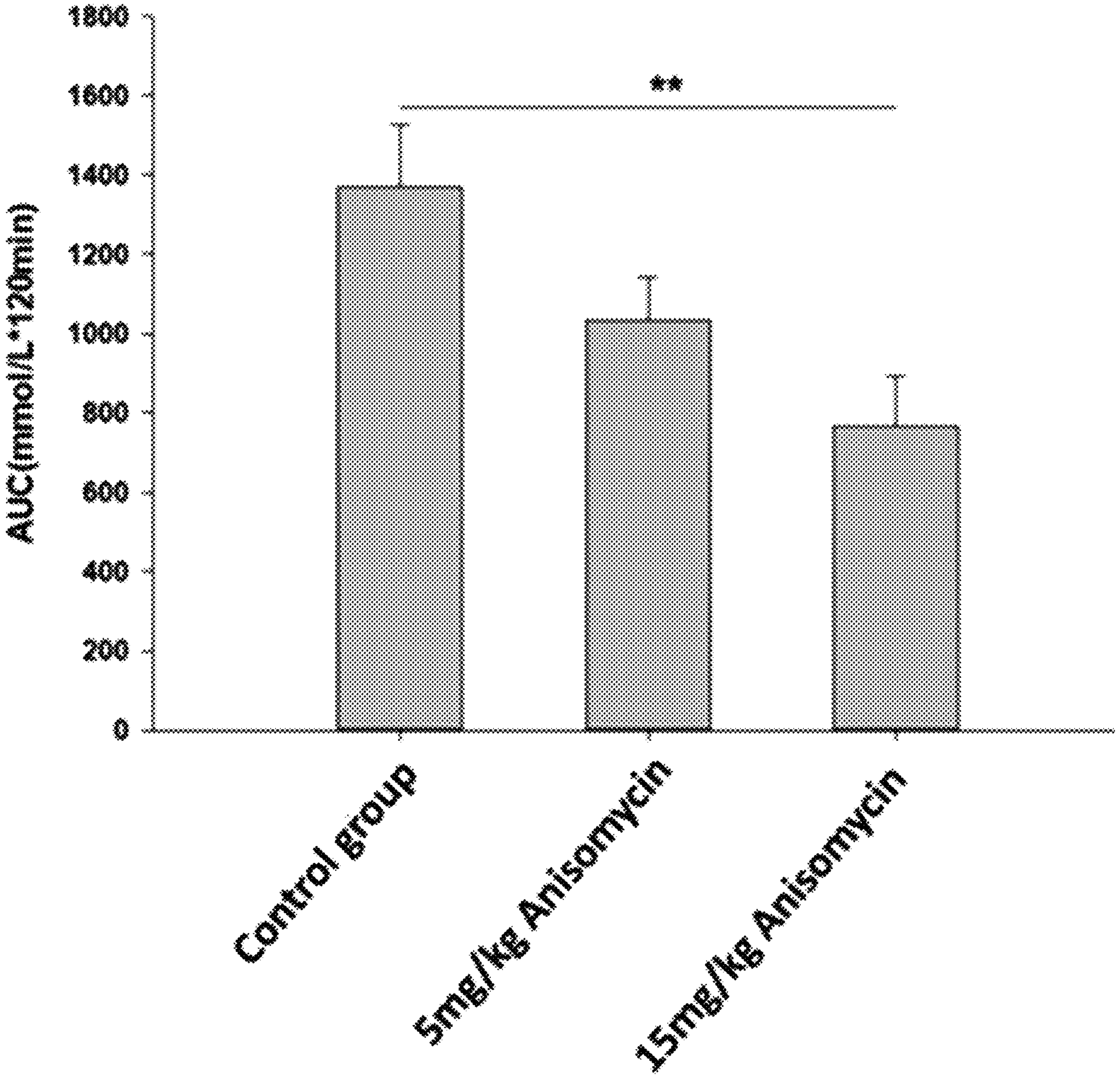
FIG. 6 B shows the area under the curve of blood glucose.

The experimental results are shown in FIGS. 6A and 6B, where FIG. 6A represents a time-varying curve graph of blood glucose in OCTT, and FIG. 6B represents an AUC graph of blood glucose. It can be seen that compared with the control group, after administrating oral glucose, tolerance of the anisomycin administration group to glucose load is improved to different extents, where 15 mg/kg anisomycin is more obvious than 5 mg/kg anisomycin in glucose reducing effect (n=7, *$p<0.05$, $p<0.01$, *$p<0.001$).

Example 4 Influence of Anisomycin Derivatives on Secretion of Rat Insulin

Compounds 1-1, 1-2, 2-1 and 2-2 are prepared in the preparation example.

Preparation before experiments: 1) there were ten groups of experiments, and Ep (Eppendorf) tubes were numbered (7 for each group); 2) a KRBH solution was prepared and was placed in an incubator for inculcation for 30 min, and the pH value was regulated with NaOH to 7.4; and 3) a sample to be tested was prepared from a 2.8 mmol/L glucose solution (2.8G), 2.8G+10 μM compound 1-1, 2.8G+10 μM compound 1-2, 2.8G+10 μM compound 2-1, 2.8G+10 μM compound 2-2, 11.1 mmol/L glucose solution (11.1G), 11.1G+10 μM compound 1-1, 11.1G+10 μM compound 1-2, 11.1G+10 μM compound 2-1 and 11.1G+10 μM compound 2-2.

Experimental steps: 1) 500 μL of 2.8G was added into each Ep tube, 5 pancreas islets (uniform in size and smooth in edge) were picked under a stereomicroscope and were placed in the Ep tube, and the Ep tube was placed in the incubator for incubation for 30 min; 2) a supernate was sucked out and abandoned with a pipette, where the pancreas islets were not sucked out, and then 500 μL of 2.8G, 2.8G+10 μM compound 1-1, 2.8G+10 μM compound 1-2, 2.8G+10 μM compound 2-1, 2.8G+10 μM compound 2-2, 11.1G, 11.1G+10 μM compound 1-1, 11.1G+10 μM compound 1-2, 11.1G+10 μM compound 2-1 and 11.1G+10 μM compound 2-2 were added into each group in sequence, and the Ep tube was placed in the incubator for incubation for 30 min; and 3) the supernate was sucked out with the pipette to the Ep tube marked in advance, the mixture was uniformly mixed, and the Ep tube was sealed and preserved at 4° C. The content of insulin in each group is detected by insulin radioimmunoassay.

The experimental results are shown in table 1, with influence of anisomycin derivatives on secretion of rat insulin. Compared with the 2.8G group, each anisomycin (10 μM) does not have the effect of promoting insulin secretion at low glucose concentration (2.8G). Compared with the 11.1G group, each anisomycin (10 μM) has the significant effect of promoting insulin secretion at the high glucose concentration (11.1G). (n=7, p<0.01, *p<0.05)

TABLE 1

| Group | n | Insulin secretion (uIU/mL) |
|---|---|---|
| 2.8G | 7 | 11.0 ± 1.2 |
| 2.8G + compound 1-1 | 7 | 12.6 ± 1.3 |
| 2.8G + compound 1-2 | 7 | 11.9 ± 1.3 |
| 2.8G + compound 2-1 | 7 | 13.0 ± 1.6 |
| 2.8G + compound 2-2 | 7 | 11.6 ± 1.0 |
| 11.1G | 7 | 43.7 ± 6.0 |
| 11.1G + compound 1-1 | 7 | 92.6 ± 8.7** |
| 11.1G + compound 1-2 | 7 | 107.3 ± 12.5** |
| 11.1G + compound 2-1 | 7 | 86.8 ± 9.4* |
| 11.1G + compound 2-2 | 7 | 96.8 ± 7.1** |

It can be known from the data in Table 1 that, in addition to the significant effect of anisomycin on promoting insulin secretion at the high blood sugar concentration, some anisomycin derivatives also have similar physiological activities. Although the present application has specifically implemented a limited number of derivatives, that is, some group substitutions have been carried out, the essence of the present invention lies in the creative discovery that anisomycin and its derivatives with the same parent nucleus have insulin-promoting effects at high blood glucose concentrations, and this effect is exerted through the stimulation of GLP-1R, indicating that this kind of compound is a kind of effective small molecule GLP-1R agonist, and the protection of the compound should not be limited to the above-mentioned specific derivatives.

The invention claimed is:

1. A method for treating diabetes in a subject, comprising administrating a therapeutically effective amount of a GLP-1R agonist to said subject, wherein the GLP-1R agonist comprises, as an active ingredient, one or more compounds selected from anisomycin, a compound of formula I, a compound of formula II, and pharmaceutically acceptable salts thereof,

I

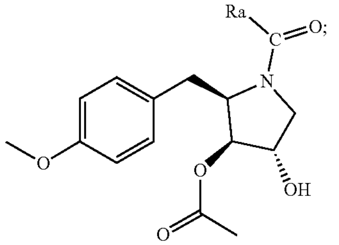

II

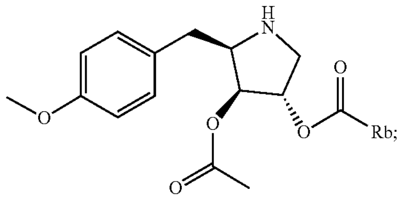

wherein Ra and Rb are independently selected from optionally substituted C1-C6 alkyl, C1-C6 alkoxyl, and C6-C20 aryl.

2. The method according to claim 1, wherein the diabetes is type 2 diabetes.

3. The method according to claim 1, wherein the dosage of the active ingredient is 0.5-50 mg/kg.

4. The method according to claim 3, wherein the dosage of the active ingredient is 5-30 mg/kg.

5. A pharmaceutical composition for treating, comprising an effective amount of an active ingredient selected from anisomycin, a compound of formula I, a compound of formula II, and pharmaceutically acceptable salts thereof,

I

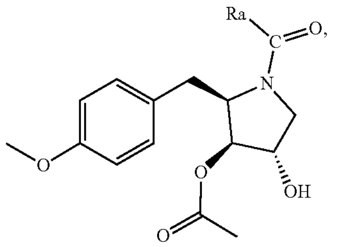

II

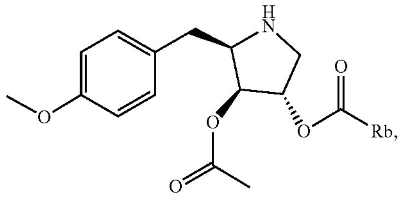

wherein Ra and Rb are independently selected from optionally substituted C1-C6 alkyl, C1-C6 alkoxyl and C6-C20 aryl; and the pharmaceutical composition further comprises metformin, a SGLT-2 inhibitor, and one or more auxiliary materials.

* * * * *